United States Patent
Gervais et al.

(10) Patent No.: US 7,560,122 B2
(45) Date of Patent: *Jul. 14, 2009

(54) PHARMACEUTICAL DOSAGE FORM BEARING PREGNANCY-FRIENDLY INDICIA

(75) Inventors: Éric Gervais, Laval (CA); Gordana Atanackovic, Dollard-des-Ormeaux (CA); Raymond Hébert, Ile Bizard (CA)

(73) Assignee: Duchesnay Inc., Laval, Quebec (CA)

( * ) Notice: Subject to any disclaimer, the term of this patent is extended or adjusted under 35 U.S.C. 154(b) by 576 days.

This patent is subject to a terminal disclaimer.

(21) Appl. No.: 10/611,803

(22) Filed: Jul. 1, 2003

(65) Prior Publication Data

US 2004/0091526 A1   May 13, 2004

(30) Foreign Application Priority Data

Jul. 5, 2002   (CA) ................................ 2392486

(51) Int. Cl.
*A61K 9/44*   (2006.01)
(52) U.S. Cl. .................. 424/467; 514/345; 514/357
(58) Field of Classification Search .................. 424/467
See application file for complete search history.

(56) References Cited

U.S. PATENT DOCUMENTS

| | | | | |
|---|---|---|---|---|
| 4,788,984 A | 12/1988 | Marsik | ..................... | 128/738 |
| 5,443,288 A | 8/1995 | Miles | ............................ | 283/2 |
| 5,457,895 A | 10/1995 | Thompson et al. | ............ | 34/296 |
| 5,531,230 A | 7/1996 | Bell | ............................ | 128/842 |
| 5,836,890 A | 11/1998 | Jackson | ..................... | 600/551 |
| 6,223,559 B1 | 5/2001 | Coleman | ................... | 63/1.13 |
| 6,226,564 B1 | 5/2001 | Stuart | ......................... | 700/231 |
| 6,340,695 B1 | 1/2002 | Gervais | ..................... | 514/345 |
| 6,352,713 B1* | 3/2002 | Kirschner et al. | ........... | 424/441 |
| D501,252 S * | 1/2005 | Gervais et al. | ............ | D24/102 |
| 2003/0124184 A1* | 7/2003 | Mezaache et al. | .......... | 424/465 |

FOREIGN PATENT DOCUMENTS

| | | |
|---|---|---|
| CA | 2050054 | 3/1992 |
| CA | 2081679 | 5/1993 |

(Continued)

OTHER PUBLICATIONS

Anke et al., "Questions about drugs: how do pregnant women solve them?" *Pharm. World Sci.*, 26(6):254-259, 1994.

(Continued)

*Primary Examiner*—Neil Levy
(74) *Attorney, Agent, or Firm*—Fulbright & Jaworski L.L.P.

(57) ABSTRACT

A pharmaceutical dosage form comprising at least one active ingredient and destined for administration to pregnant women. The pharmaceutical dosage form bears pregnancy-friendly indicia apt to improve patient compliance with medically recommended dosage regimen resulting in improved product effectiveness. The pregnancy-friendly indicia is also apt to diminish the incidence of erroneous dispensing of or erroneous ingestion of pharmaceutical dosage forms not intended for pregnant women. Also disclosed is a method for achieving improved patient compliance resulting in improved product effectiveness. Also disclosed is a method for diminishing the incidence of erroneous dispensing of or erroneous ingestion of dosage forms not intended for pregnant women. Said methods comprising providing a pharmaceutical dosage form, intended for use by pregnant women, bearing pregnancy-friendly indicia apt to graphically distinguish dosage forms intended to be used during pregnancy from others.

1 Claim, 1 Drawing Sheet

FOREIGN PATENT DOCUMENTS

| CA | 2310069 | 6/1999 |
|----|---------|--------|
| CA | 2321991 | 9/1999 |
| CA | 2280279 | 2/2000 |
| CA | 2078578 | 2/2002 |
| EP | 1 149 572 | 10/2001 |
| WO | WO 97/48384 | 12/1997 |
| WO | WO 2004/004694 | 1/2004 |

OTHER PUBLICATIONS

Czeizel and Dudas, "Prevention of the first occurrence of neural tube defects by periconceptional vitamin supplementation," *New England J. Med.*, 327:1832-1835, 1992.

Einarson et al., "Abrupt discontinuation of psychotropic drugs during pregnancy: fear of teratogenic risk and impact of counselling," *J. Psychiatry Neurosci.*, 26(1):44-48, 2001.

Koren and Pastuszak, "Prevention of unneccessary pregnancy terminations by counseling women on drug, chemical and radiation exposure during the first trimester," *Teratology*, 41(6):657-661, 1990.

Matsuri, "Drug compliance in pediatrics. Clinical and research issues," *Ped. Clin. N. Amer.*, 44(1):1-14, 1997.

Mazzotta et al., "Factors associated with elective termination of pregnancy among Canadian and American women with nausea and vomiting of pregnancy," *J. Psychosom Obstet. Gynecol.*, 22(1):7-12, 2001.

Olesen et al., "Do pregnant women report use of dispensed medications?" *Epidemiology*, 12(5):497-501, 2001.

Pastuszak et al., "The effectiveness of preconceptional counseling on women's compliance with folic acid supplementation, maternal-fetal toxicology, A clinician's guide," 3$^{rd}$ Edition, pp. 141-149, 2001.

Pole et al., "Drug labeling and risk perceptions of teratogenicity: A survey of pregnant Canadian women and their health professionals," *J. Clin. Pharmacol.*, 40:573-577, 2000.

Bishai et al., "The efficacy and cafety of Diclectin (R) (doxylamine/pyridoxine) for nausea and vomiting of pregnancy," *Today's Therapeutic Trends*, 17(2):167-179, 1999.

Muno, "Broadening utility of tablet and capsule imprints," *Journal of Pharmacy Practice*, 13(2);130-140, 2000.

Pedersen, "Tablet tooling: design, maintenance and troubleshooting," *Pharmaceutical Technology Europe*, 11(2):22-28, 1999.

"Continuing need to prevent exposures during pregnancy to medications known to cause birth defects," *CDC Media Relations Press Release*, Aug. 17, 2001.

Daniel et al., "Interpretations of a teratogen warning symbol," *Teratology*, 64(3):148-153, 2001.

Pearson, "Proposed switch of Acyclovir from prescription to over-the-counter status," *National Women's Health Network*, May 19, 1994.

Pole et al., "Drug labeling and risk perceptions of teratogenicity: a survey of pregnant Canadian women and their health professionals," *J. Clin. Pharmacol.*, 40(6):573-577, 2000.

* cited by examiner

PHARMACEUTICAL DOSAGE FORM BEARING PREGNANCY-FRIENDLY INDICIA

This Application claims priority to co-pending Canadian Application No. CA/2,392,486 filed on Jul. 5, 2002

FIELD OF THE INVENTION

The present invention relates to pharmaceutical dosage forms intended for use during pregnancy.

BACKGROUND OF THE INVENTION

During pregnancy a variety of medical conditions require treatment with therapeutic agents. For instance, in Canada, excessive nausea and vomiting, possibly leading to hyperemesis gravidarum, are routinely treated with the prescription drug Diclectin® which contains a mixture in equal amounts of two active ingredients, namely pyridoxine HCl and doxylamine succinate.

Other conditions, pre-existing or developed during pregnancy, for example: diabetes, hypertension, blood cloths, depressive illness and heart disease are also commonly treated with prescription drugs.

In the case of pre-existing medical conditions numerous studies have shown that women have a tendency to abruptly stop taking their medications upon learning of the pregnancy, due to the perceived fear of birth defects[1]. In many cases, the risk to the health of the expectant mother and her baby is much higher if she stops or reduces her treatment than if she keeps taking the required medications.

Because of this perceived risk of harm to the fetus, otherwise known as the teratogenic risk, it is common for expectant mothers to discontinue taking a prescribed drug or to voluntarily diminish the prescribed dosage regimen. This often leads to dosage levels below therapeutic ranges in turn leading patients and the medical community to incorrectly conclude that a particular drug is clinically ineffective.

Discontinuing or altering drug therapy, often against competent medical prescription, may have grave consequences indeed. The health of the expectant mother and vicariously of the fetus may be put at great risk because of poor compliance with competent medical prescription. In many instances, the teratogenic risks must be weighed against the risk of catastrophic illness or worsening condition on the part of the expectant mother.

Even discounting the particular problem of patient compliance during pregnancy, drug therapy patient compliance is a widespread and difficult problem in the medical community. Non-compliance with prescribed drug dosage regimen is a huge health problem for patients in general. For example, it is estimated that less than 25% of outpatients will complete a 10 day course of antibiotic therapy for a strep throat or otitis media.

Matsui[2] described that non-compliance with prescribed medication regimens may take many forms, including failure to fill the prescription, incorrect dosage, improper dosing interval, and premature discontinuation of the drug. Of course, the problem of non-compliance is magnified during pregnancy due to the importance of fetal safety.[3]

Whenever women delay or discontinue use of medications during pregnancy due to fears related to fetal safety, the result may be a worsening of the condition and hospitalisation with use of multiple drug therapy. Furthermore, depending of the underlying condition, the worsening of the condition has serious consequences even including suicidal ideation. Einarson showed in her study[1] on abrupt discontinuation of psychotropic drugs during pregnancy due to teratogenic fears, that 70.3% of women reported physical and psychological adverse effects to the point that 29.7% reported suicidal ideation (one third of them were hospitalised).

Despite these appalling statistics, the perception of the expectant mother remains shrouded by well-known errors of the past such as the widely publicized cases of thalidomide-induced fetal malformations. The graphic evidence of birth defects attributed to Thalidomide exposure during early pregnancy has left a teratogenicity stigma on all medications. Hence, it is commonly thought that all medications are to be avoided during pregnancy. In the study entitled "*Prevention of Unnecessary Pregnancy Terminations by Counselling Women of Drug, Chemical, and Radiation Exposure During the First Trimester*", (1990)[4], Koren showed that pregnant women exposed to drugs that are known to be non teratogenic, still perceive that their born-to-be baby has a 24% chance to suffer a major birth defect. This is about the same risk as an intra-uterine exposure to Thalidomide.

Scientific studies aimed at measuring the risk of drugs during pregnancy and patient education and counseling have so far been at the forefront of efforts to achieve better patient compliance with medical prescription.

However, even in the case of drugs having an extensively demonstrated record of fetal innocuousness, such as Diclectin® used to curb nausea and vomiting, the perception of latent risk remains. This perception of risk is of course carried over from the negative experiences of thalidomide which was also prescribed for nausea and vomiting during pregnancy and which was also provided as an oral dosage form. However, in reality, the active ingredient thalidomide and the active ingredients of Diclectin®, namely pyridoxine HCl and doxylamine succinate are completely unrelated. The risk perception carried-over from thalidomide is made apparent from patient compliance inquiries. Patient compliance with a medically prescribed dosage regimen of Diclectin® is clearly below what is recommend in the medical profession.

Even physicians and pharmacists are anxious about their liability associated with prescription or dispensing of medications to pregnant women. In the study by Pole[5], it was shown that even health care professionals, after reading four different labels (all of them stating that drug is safe to be used in pregnancy), have evaluated these labels, as bearing a residual risk. They were unable to fully perceive or accept that medication is safe to be used in pregnancy. Patients, physicians and pharmacists are also worried about erroneous ingestion or dispensing of drugs not intended for use during pregnancy.

Despite the enormous volume of scientific evidence supporting Diclectin® harmlessness to the fetus, pregnant women persistently do not follow their physician's recommendation as to the adherence to Diclectin® dosage regimen. In most cases, women voluntarily reduce the dosage by half. In fact, they do not comply with the proper dosage regimen for Diclectin® to the point that some woman and some physicians believe that the medication is not effective. Therefore, non-compliance often results in a perception of product effectiveness failure.

Due to non-compliance with medical prescription, patients using less than prescribed amounts of Diclectin® will often find themselves in sub-therapeutic state. This prevents the medication from being effective and may aggravate the mother's condition to the point of developing hyperemesis gravidarum (HG). HG is the most severe end of nausea and vomiting during pregnancy, when a pregnant woman suffers from loss of more than 5% of her pre-pregnancy body weight, dehydration, acid-base disturbances, ketonuria and electrolyte imbalance. At this stage, physicians use intravenous medications that are often not recognised for safe use during pregnancy in order to control maternal condition. The use of these medications poses an unnecessary risk to the fetus. If this last resort medication appears to be ineffective due to the deterioration of the woman's condition, a therapeutic abortion may even be considered[6].

In order to diminish potential for birth defects a vitamin intake is now medically recommended during pregnancy. For example, clinical evidence shows that taking folic acid before conception and during the first trimester of pregnancy may prevent up to 72% of the congenital abnormalities spina bifida and anencephaly[7]. Despite this, pregnant women are generally non compliant with recommended folic acid intake treatment thus putting an unborn child at an increased risk of major birth defect.

The situation is even worse if pregnant woman has been on a drug therapy that interferes with folic acid receptors (e.g., phenobarbital, phenytoin, carbamazepine, valproic acid). In this case, a pregnant woman is even at greater risk for having a baby with birth defect if she is not compliant.

Thus there remains an important need for innovative solutions to achieve better patient compliance of vitamins or drugs recommended for use during pregnancy.

OBJECTS OF THE INVENTION

An object of the present invention is therefore to provide an improved oral dosage form for, inter alia, achieving better patient compliance with vitamins or drugs intended for use during pregnancy.

Another object is to provide a method for improving patient compliance of pregnant women by diminishing their perception of teratogenic risk and by direct implication to improve product effectiveness of dosage forms containing at least one active ingredient and intended for use by pregnant women.

A further object is to provide a method for diminishing the incidence of erroneous ingestion by pregnant women or of erroneous dispensing by pharmacists of therapeutic agents not prescribed to said pregnant women.

SUMMARY OF THE INVENTION

More specifically, in accordance with the present invention, there is provided a pharmaceutical dosage form comprising at least one active ingredient, such as for example a vitamin supplement or a synergistic combination of pyridoxine HCl and doxylamine succinate, and destined for administration to pregnant women, the pharmaceutical dosage form bearing pregnancy-friendly indicia. In a preferred embodiment the pregnancy-friendly indicia is in the shape of a graphical illustration of a pregnant woman applied to the dosage form itself or to its packaging. In a most preferred embodiment, the dosage form is destined for oral administration.

Also provided is a method of diminishing the perception of teratogenic risk among pregnant women taking a pharmaceutical dosage form containing at least one active ingredient. The method comprising providing said pharmaceutical dosage form bearing pregnancy-friendly indicia, preferably in the shape of a graphical illustration of a pregnant woman applied to the dosage form itself or to its packaging.

Also provided is a method of improving patient compliance of pregnant women with medically recommended dosage regimen of at least one active ingredient. The method comprising providing a pharmaceutical dosage form bearing pregnancy-friendly indicia. Improving patient compliance also leads to improved product effectiveness because product effectiveness is linked to patient compliance. Thus, the method of the present invention also leads to improved product effectiveness.

Also provided is method of diminishing the incidence of erroneous ingestion by pregnant women or of erroneous dispensing by pharmacists of therapeutic agents not prescribed to said pregnant women. The method comprising providing a pharmaceutical dosage form comprising at least one active ingredient prescribed to said pregnant women, the dosage form bearing pregnancy-friendly indicia apt to graphically distinguish dosage forms intended to be used during pregnancy from others.

Other objects, advantages and features of the present invention will become more apparent upon reading of the following non-restrictive description of preferred embodiments thereof, given by way of example only with reference to the accompanying drawing.

DESCRIPTION OF THE PREFERRED EMBODIMENT

Figure 1:
FIG. 1 is a pictorial representation of an improved oral dosage form in accordance with the present invention and bearing a visible indicia apt to achieve improved patient compliance.

The main object of the present invention is therefore to provide an improved oral dosage form for achieving better patient compliance with drugs prescribed for use during pregnancy. This objective is surprisingly and effectively achieved by applying pregnancy-friendly indicia on the dosage form. Dosage form is understood to encompass its packaging. By "pregnancy-friendly" indicia is meant any graphical or textual representation apt to be easily recognized as indicative of a safe medication for taking during pregnancy.

In a most preferred embodiment, the pregnancy-friendly indicia are a graphical representation of the profile of a pregnant woman having a hand resting on her stomach region. Such graphical representation is illustrated in FIG. 1 and has a particularly comforting effect on expectant mothers and have been statistically shown to substantially lower the perception of teratogenic risk and consequently lead to elevated patient compliance. Such evidence is presented in the examples provided below.

EXAMPLE 1

A study was conducted with 12 pregnant women. This study was aimed at testing if pregnancy-friendly indicia such as the indicia illustrated in FIG. 1 may have a positive impact by reducing the perception of teratogenic risk of a drug taken during pregnancy, and if it is the case, which kind of design is most effective in improving patient compliance.

Different designs of pregnancy-friendly indicia were printed on tablets. This aim was to ascertain if, when used, those indicia would increase the patients' confidence in taking the tablet during pregnancy by reducing the perception of teratogenic risk. Diminishing the perception of teratogenic risk would consequently improve patient compliance and as a result achieve better treatment effectiveness.

The study revealed while all pregnancy-friendly indicia are helpful at diminishing the perception of teratogenic risk, the most preferred graphical representation is that of FIG. 1. The graphical representation shown in FIG. 1 would indicate in a clear and precise fashion that the medication has been specifically designed for the pregnant woman.

This surprising positive effect on patient compliance would of course translate itself in the effectiveness of a vitamin or drug treatment and a concurrent reduction of medical complications for the pregnant woman and the fetus.

EXAMPLE 2

To further validate the findings disclosed in Example 1, an observational, prospective survey on pregnant women in family practice offices and obstetrician offices was conducted. The statistical tool used for measuring the objective of the study (how reassured about fetal safety woman feels taking one or the other tablet once prescribed to them) was a validated scientific tool for subjective measurements: a visual analog scale (VAS) from 1-5 (1 being the least safe and 5 being the most safe). Patients were told that the prescribed drug, in tablet form, was safe for use in pregnancy and were asked to label on the VAS how reassured about fetal safety they felt when taking the tablet. They were shown two different tablets, one plain white and the other white with the illustration of FIG. 1 applied to the tablet.

Data was collected from 132 pregnant women and the results are shown in the table below:

| Test: Dual-Sample Assuming Equal Variances | | |
|---|---|---|
| | Plain White tablet | Tablet with pregnancy-friendly indicia as per FIG. 1 |
| Observations | 132 | 132 |
| Mean Risk Perception | 2,5227 | 3,6969 |
| Variance | 1,2132 | 1,3120 |
| P (T <= t) one-tail | | P < 0.0001 |

Teratogenic Risk Perception on Scale of 1 to 5 with 1 being greatest risk perception.

The study clearly showed superiority of the tablet with a printed pregnant woman concerning the perception of the teratogenic risk (results were statistically significant with P<0.0001). The P value of 0.0001 signifies that the result of this study as 1/10,000 chance to be the result of chance only. If we repeat this study 10,000 times, in 9,999 cases, the same results would be obtained. Usually P<0.05 is recognized as medically significant.

Thus, in the sample group of 132 pregnant women, 23.4% felt more reassured about the fetal safety of taking the tablet with a printed pregnant woman as shown in FIG. 1, than a plain white tablet.

Of course, these results would translate themselves directly into improved patient compliance by a margin of at least 23.4%. Thus, a strong conclusion emerges that the presence of pregnancy-friendly indicia on a vitamin or drug to be taken during pregnancy will significantly reduce teratogenic risk perception and by the same token improve patient compliance with prescribed dosage regimen.

Although the present invention has been described hereinabove by way of preferred embodiments thereof, it can be modified, without departing from the spirit and nature of the subject invention as defined in the appended claims. More specifically, the exact appearance of pregnancy-friendly indicia is variable with the understanding that some indicia will induce greater patient compliance than others. Also, it is to be understood that although examples were given in relation to oral tablets, other pharmaceutical dosages forms are of course covered by the present invention. Thus, pregnancy-friendly indicia may appear on the actual dosage form, such as tablet, sugar coated tablet, sublingual tablet, caplet, capsule, gel capsule, chewable tab, pill, suppository, powder, vial, ampoule, pre-filled syringe, nasal spray, pastille, syrup, drops, vaginal ovule, subcutaneous implant, transdermal gel, transdermal patch, transmucausal strip, pouch, or may also appear on the packaging and labeling of the dosage form.

REFERENCES

1. Einarson A., Selby P., Koren G., *Abrupt discontinuation of psychotropic drugs during pregnancy: fear of teratogenic risk and impact of counseling*, J. psychiatry Neurosci 2001; 26(1): 44-48
2. Matsui D., *Drug compliance in pediatrics: Clinical and research issues*. Ped Clin N Amer 1997;44(1):1-14
3 Anke M., et al., *Questions about drugs: how do pregnant women solve them*? Pharm world Sci 1994 Dec. 2;16(6): 254-9;
    and
    Olesen C., Sondergaard C., *Do Pregnant Women Report Use of Dispensed Medications?*, Epidemiology 2001; 12(5):497-501
4. Koren G., Pastuszak A., *Prevention of Unnecessary Pregnancy Terminations by Counselling Women on Drug, Chemical, and Radiation Exposure During the First Trimester*, Teratology 1990;41(6):657-61
5. Pole M., Einarson A., Pairaudeau N.& al., *Drug Labeling and Risk Perceptions of Teratogenicity: A Survey of Pregnant Canadian Women and Their Health Professionals*, J Clin. Pharmacol. 2000;40: 573-577
6. Mazzotta P., Stewart D., Koren G., Magee L A. *Factors associated with elective termination of pregnancy among Canadian and American women with nausea and vomiting of pregnancy*. J. Psychosom Obstet. Gynecol. 2001;22(1): 7-12
7 Czeizel A E, Dudas I: Prevention of the first occurance of neural tube defects by periconceptional vitamin supplementation. N Eng J Med 1992; 327:1832-1835;
    and
    Pastuszak A., Bhatia D., Okotore B., Koren G., *The Effectiveness of Preconceptional Counseling on Women's Compliance with Folic Acid Supplementation*, Maternal-Fetal Toxicology, A Clinician's Guide, Third-Edition, 2001:141-149

What is claimed is:

1. A patient dosage regimen compliance improving pharmaceutical tablet destined for administration to pregnant women, said pharmaceutical tablet containing a drug combination for use against excessive nausea and vomiting, said drug combination comprising therapeutically effective amounts of doxylamine succinate and pyridoxine hydrochloride, said pharmaceutical tablet further comprising a graphical representation of a pregnant woman applied to the tablet surface, said graphical representation being visible to the naked eye.

* * * * *